United States Patent [19]
Cozzi et al.

[11] Patent Number: 5,283,254
[45] Date of Patent: * Feb. 1, 1994

[54] 2-(IMIDAZOL-1-YL)-2-BENZYLETHYLIDI-ENE-AMINOXYALKANOIC ACID DERIVATIVES

[75] Inventors: Paolo Cozzi; Maria Menichincheri, both of Milan; Arsenia Rossi, Dalmine; Corrado Ferti, Barlassina; Patricia Salvati, Arese, all of Italy

[73] Assignee: Farmitalia Carlo Erba S.r.l., Milan, Italy

[*] Notice: The portion of the term of this patent subsequent to Jun. 2, 2009 has been disclaimed.

[21] Appl. No.: 917,245

[22] Filed: Jul. 22, 1992

[30] Foreign Application Priority Data

Jul. 30, 1991 [GB] United Kingdom ............ 9116470.7

[51] Int. Cl.$^5$ ................ A61K 31/415; C07D 233/60
[52] U.S. Cl. .................................. 514/399; 548/336.1
[58] Field of Search ............................ 548/341, 336.1; 514/399

[56] References Cited

FOREIGN PATENT DOCUMENTS 3220183  5/1982  Fed. Rep. of Germany .

OTHER PUBLICATIONS

Derwent Abstract of WO 91/13062, Farmitalia Carlo Erba, published Sep. 5, 1991.
Derwent Abstract of DE 3334220, Bayer AG, published on Nov. 4, 1985.
Cover page and Derwent Abstract of EP 0,028,346, Bayer AG, published on May 20, 1981.
Cover Page and Derwent Abstract of European, 0,065,107, Bayer AG, published on Nov. 24, 1988.
Derwent Abstract of EP 0132771, Hoechst AG, published on Feb. 13, 1985.
Derwent Abstract of DE 3548085, Bayer AG, published on Jul. 2, 1987.
Derwent Abstract of EP 0158299, Merz & Co., published on Oct. 16, 1985.

*Primary Examiner*—Patricia L. Morris
*Attorney, Agent, or Firm*—Nikaido, Marmelstein, Murray & Oram

[57] ABSTRACT

The present invention relates to 2-(imidazol-1-yl)-2-benzylethylidene-aminoxyalkanoic acid derivatives of formula (I)

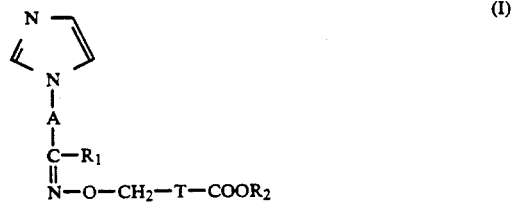

wherein
A is a divalent group of formula

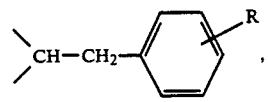

in which
R is hydrogen, halogen, $CF_3$, $C_1$-$C_4$ alkoxy, $C_1$-$C_4$ alkylsulfonyl or cyano;
$R_1$ is a) phenyl unsubstituted or substituted by halogen, $C_1$-$C_4$ alkoxy, $CF_3$ or $C_1$-$C_4$ alkylsulfonyl; b) cyclohexyl; or c) a straight or branched $C_1$-$C_6$ alkyl group;
T is a branched or straight $C_3$-$C_5$ alkylene chain;
$R_2$ is hydrogen or $C_1$-$C_4$ alkyl, and the pharmaceutically acceptable salts thereof, which are useful as selective inhibitors of thromboxane $A_2$ ($TxA_2$) synthesis.

3 Claims, No Drawings

2-(IMIDAZOL-1-YL)-2-BENZYLETHYLDIENE-AMINOXYALKANOIC ACID DERIVATIVES

In International Patent Application PCT/EP91/00351 new 1-(alkoxy-iminoalkyl)imidazole derivatives with valuable biological properties have been described.

Now we have found that new compounds closely related to such 1-(alkoxy-iminoalkyl)imidazole derivatives and a selected class of the compounds previously disclosed in the above patent application are surprisingly endowed with higher biological activity.

Accordingly, the present invention relates to 2-(imidazol-1-yl)-2-benzylethylidene-aminoxyalkanoic acid derivatives of formula (I), as herein defined, to the pharmaceutically acceptable salts thereof, to a process for their preparation, to pharmaceutical compositions comprising them and to their use as therapeutic agents.

The present invention provides compounds having the general formula (I)

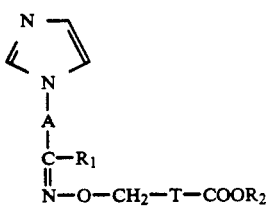

wherein
A is a divalent group of formula

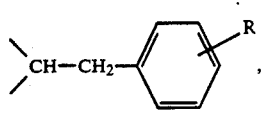

in which
R is hydrogen, halogen, $CF_3$, $C_1$-$C_4$ alkoxy, $C_1$-$C_4$ alkylsulfonyl or cyano;
$R_1$ is a) phenyl unsubstituted or substituted by halogen, $C_1$-$C_4$ alkoxy, $CF_3$ or $C_1$-$C_4$ alkylsulfonyl; b) cyclohexyl; or c) a straight or branched $C_1$-$C_6$ alkyl group;
T is a branched or straight $C_3$-$C_5$ alkylene chain;
$R_2$ is hydrogen or $C_1$-$C_4$ alkyl; and the pharmaceutically acceptable salts thereof.

The compounds of formula (I), and the salts thereof, in which A, T, $R_1$ and $R_2$ are as defined above and R is $C_1$-$C_4$ alkoxy, cyano or $C_1$-$C_4$ alkylsulfonyl have never been disclosed before. The other compounds of formula (I), as stated above, are a selected class of those described in the above mentioned U.K. patent applications, however none of such compounds has therein specifically been mentioned.

The invention also includes within its scope all the possible isomers, stereoisomers and their mixtures and the metabolites and the metabolic precursors or bioprecursors of the compounds of formula (I).

In particular the compounds of formula (I) exhibit either E or Z isomerism about the oximic double bond. Both the single E and Z isomers of the compounds of formula (I) and their mixtures are also included within the scope of the present invention.

A $C_1$-$C_6$ group is preferably a $C_1$-$C_4$ alkyl group.

A $C_1$-$C_4$ alkyl group is e.g. methyl, ethyl, propyl, isopropyl, butyl or tert.butyl, more preferably methyl or butyl.

A $C_1$-$C_4$ alkoxy group is e.g. methoxy, ethoxy, propoxy, isopropoxy, butoxy or tert.butoxy, preferably methoxy, ethoxy or propoxy.

A halogen atom is suitably bromine, chlorine or fluorine, preferably it is bromine or fluorine.

A $C_1$-$C_4$ alkylsulfonyl group is preferably a methyl- or ethylsulfonyl, in particular methylsulfonyl, group.

T is preferably a divalent group chosen from —CH$_2$—CH$_2$—CH$_2$—,

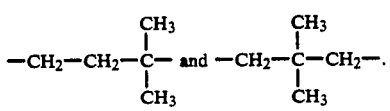

Pharmaceutically acceptable salts of the compounds of the invention include acid addition salts, with inorganic, e.g. nitric, hydrochloric, hydrobromic, sulphuric, perchloric and phosphoric acids, and organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethyl-amine.

As stated above the present invention also includes within its scope pharmaceutically acceptable bioprecursors (otherwise known as pro-drugs) of the compounds of formula (I), i.e. compounds which have a different formula to formula (I) above but with nevertheless upon administration to a human being are converted directly or indirectly in vivo into a compound of formula (I).

Examples of specific compounds according to the present invention are the following compounds, either as Z- or E-isomers or Z,E-mixtures of said isomers:
(±)-5-[1-phenyl-2-(imidazol-1-yl)-2-(4-fluorobenzyl)ethylidene]aminoxypentanoic acid;
(±)-5-[1-phenyl-2-(imidazol-1-yl)-2-(4-chlorobenzyl)ethylidene]aminoxypentanoic acid;
(±)-5-[1-cyclohexyl-2-(imidazol-1-yl)-2-(3-fluorobenzyl)ethylidene]aminoxypentanoic acid;
(±)-5-[1-cyclohexyl-2-(imidazol-1-yl)-2-(4-methoxybenzyl)ethylidene]aminoxypentanoic acid;
(±)-5-[1-cyclohexyl-2-(imidazol-1-yl)-2-(4-trifluoromethylbenzyl)ethylidene]aminoxypentanoic acid;
(±)-5-[1-cyclohexyl-2-(imidazol-1-yl)-2-(3-chlorobenzyl)ethylidene]aminoxypentanoic acid;
(±)-5-[1-(4-fluorophenyl)-2-(imidazol-1-yl)-2-(3-chlorobenzyl)ethylidene]aminoxypentanoic acid;
(±)-5-[1-(3-trifluoromethylphenyl)-2-(imidazol-1-yl)-2-(4-fluorobenzyl)ethylidene]aminoxypentanoic acid;
(±)-5-[1-(3-methylsulfonylphenyl)-2-(imidazol-1-yl)-2-(3-fluorobenzyl)ethylidene]aminoxypentanoic acid;
(±)-5-[1-(4-methylsulfonylphenyl)-2-(imidazol-1-yl)-2-(4-fluorobenzyl)ethylidene]aminoxypentanoic acid;
(±)-5-[1-cyclohexyl-2-(imidazol-1-yl)-2-benzylethylidene]-2,2-dimethylaminoxypentanoic acid;
(±)-5-[1-cyclohexyl-2-(imidazol-1-yl)-2-benzylethylidene]-3,3-dimethylaminoxypentanoic acid;
(±)-5-[1-cyclohexyl-2-(imidazol-1-yl)-2-(4-methylsulfonylbenzyl)ethylidene]aminoxypentanoic acid;

(±)-5-[1-(4-fluorophenyl)-2-(imidazol-1-yl)-2-(4-methylsulfonylbenzyl)ethylidene]aminoxypentanoic acid;
(±)-5-[1-phenyl-2-(imidazol-1-yl)-2-benzylethylidene]-3,3-dimethylaminoxypentanoic acid;
(±)-5-[1-(3-trifluoromethylphenyl)-2-(imidazol-1-yl)-2-benzylethylidene]aminoxypentanoic acid;
(±)-5-[1-phenyl-2-(imidazol-1-yl)-2-benzylethylidene]-2,2-dimethylaminoxypentanoic acid;
(±)-5-[1-(4-methoxyphenyl)-2-(imidazol-1-yl)-2-(4-fluorobenzyl)ethylidene]aminoxypentanoic acid;
(±)-5-[1-n-hexyl-2-(imidazol-1-yl)-2-benzylethylidene]aminoxypentanoic acid;
(±)-5-[1-methyl-2-(imidazol-1-yl)-2-benzylethylidene]aminoxypentanoic acid;
(±)-5-[1-methyl-2-(imidazol-1-yl)-2-(4-fluorobenzyl)ethylidene]aminoxypentanoic acid;
(±)-5-[1-ethyl-2-(imidazol-1-yl)-2-benzylethylidene]aminoxypentanoic acid;
(±)-5-[1-propyl-2-(imidazol-1-yl)-2-benzylethylidene]aminoxypentanoic acid;
(±)-5-[1-(4-chlorophenyl)-2-(imidazol-1-yl)-2-(4-flurobenzyl)ethylidene]aminoxypentanoic acid; and the pharmaceutically acceptable salts thereof.

The compounds of the invention and the salts thereof can be obtained by a process comprising:
a) reacting an oxime of formula (II) or a salt thereof

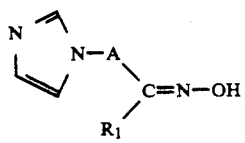

(II)

wherein
A and R$_1$ are as defined above, with a compound of formula (III)

Y—CH$_2$—T—COR$_2$   (III)

wherein
T and R$_2$ are as defined above and Y is a leaving group; or b) reacting an oxime of formula (II) as defined above or a salt thereof with a lactone of formula (IV)

(IV)

wherein
T is as defined above, thus obtaining a compound of formula (I) in which R$_2$ is —OH; or c) reacting a compound of formula (V)

(V)

wherein
A and R$_1$ are as defined above, with a compound of formula (VI)

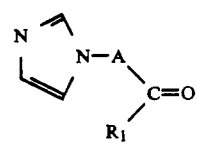

H$_2$N—O—CH$_2$—T—COR$_2$   (VI)

wherein
T and R$_2$ are as defined above; or
d) reacting a compound of formula (V), as defined above, with a compound of formula (VII)

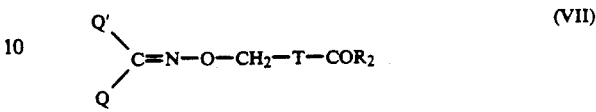

(VII)

wherein
T and R$_2$ are as defined above and each of Q and Q' is independently hydrogen, lower alkyl or phenyl; and if desired converting a compound of formula (I) into another compound of formula (I), and/or, if desired converting a compound of formula (I) into a salt thereof, and/or, if desired, converting a salt of a compound of formula (I) into a free compound, and/or, if desired, separating a mixture of isomers of a compound of formula (I) into the single isomers, and/or, if desired, altering by isomerization on the oxime double bond the ratio of E- and Z-isomers of a compound of formula (I) in a mixture thereof so as to obtain a different ratio of such isomers, and/or, if desired, converting by isomerization on the oxime double bond a pure E-isomer of a compound of formula (I) either into a pure Z-isomer thereof or into a mixture of E- and Z-isomers thereof; and/or if desired converting by isomerization on the oxime double bond a pure Z-isomer of a compound of formula (I) either into a pure E-isomer or into a mixture of E- and Z-isomers thereof.

A salt of a compound of formula (II) is for example an alkali metal salt, in particular a sodium or lithium salt. A salt of a compound of formula (II) may be obtained according to known methods, for example a compound of formula (II) can be reacted with an alkali metal hydride, preferably NaH, in an inert organic solvent, e.g. dimethylformamide. The leaving group Y in a compound of formula (III) is for example a halo group, in particular a chloro or bromo group, or a residue of an active ester group, in particular mesyl or tosyl.

The reaction of a compound of formula (II), or a salt thereof, with a compound of formula (III) can be carried out according to known methods, for example in the presence of an inert reaction organic solvent, e.g. dimethylformamide, dimethylsulfoxide, tert.butanol or benzene, and by addition of an appropriate basic agent e.g. an alkali metal carbonate, in particular sodium carbonate, or sodium hydride or potassium tert.butylate, at a temperature ranging from about 0° C. to reflux temperature.

The reaction of a compound of formula (II) or a salt thereof, as defined above, with a compound of formula (IV) may be performed according to known methods. For example such reaction can be carried out by following the same reaction conditions described as to the reaction of a compound of formula (II), or a salt thereof, with a compound of formula (III). The reaction of a carbonyl compound of formula (V) with an aminooxy derivative of formula (VI) can be carried out, for example, by dissolving the carbonyl compound in a reaction inert solvent, e.g. water, a lower alkanol, in particular ethanol, dioxane, tetrahydrofuran, an aromatic hydrocarbon, in particular benzene, toluene or xylene, or mixtures of such solvents, and by adding an appropriate basic agent, for example an alkali metal hydroxide, in particular sodium or potassium hydroxide, a carbonate or hydrogen carbonate, in particular the sodium and potassium ones, or an organic basic agent, e.g. a tertiary amine or pyridine.

When one or both of Q and Q' in a compound of formula (VII) is lower alkyl, it is for example $C_1$-$C_4$ alkyl, in particular methyl or ethyl.

Also the reaction of a compound of formula (V) with a compound of formula (VII) can be carried out according to known methods. For example such reaction can be performed in an inert reaction solvent, e.g. acetonitrile or acetic acid, and if required in the presence of a mineral acid, e.g. sulphuric or hydrochloric acid, at temperatures ranging from room temperature to reflux temperature.

The conversion of a compound of formula (I) into another compound of formula (I) can be carried out by methods known in themselves. For example, a compound of formula (I) containing an esterified carboxy group can be converted into the corresponding free carboxylic acid by known methods.

A compound of formula (I) containing a free carboxy group can be converted into a corresponding esterified carboxy derivative.

Such esterification reaction can be carried out according to known methods, preferably via an intermediate reactive derivative of the carboxylic acid, which may be isolated or not, by reaction with the appropriate $C_1$-$C_4$ alkanol. The reaction can be carried out in a customary solvent e.g. benzene or toluene, or in the presence of an excess of the alkanol itself.

The temperature reaction may range from about 10° C. to about 50° C. Intermediate reactive derivatives of the carboxylic acid may be for example acidic halides, e.g. the chloride, mixed anhydrides e.g. ethoxycarbonyl or tert. butyloxy anhydrides, or a suitable reactive intermediate obtained in situ e.g. by reaction with a diimide e.g., dicyclohexylcarbodiimide, or carbonyl diimidazole.

The optional salification of a compound of formula (I) as well as the conversion of a salt into the free compound and the separation of a mixture of isomers into the single isomers may be carried out by conventional methods.

For example the separation of a mixture of geometric isomers, e.g. Z- and E-isomers, may be carried out by fractional crystallization from a suitable solvent or by chromatography, either column chromatography or high pressure liquid chromatography.

The optional isomerization on the oxime double bond in a compound of formula (I), which is an equilibrium reaction, can be performed according to known methods; preferably in the presence of a mineral acid e.g. hydrochloric acid and/or by heating.

The oximes of formula (II) can be obtained according to known methods. For example a') by reaction of a compound of formula (V), as defined above, with hydroxylamine or an acid addition salt thereof, e.g. the sodium or potassium salt, or b') by reaction of an oxime of formula (VIII)

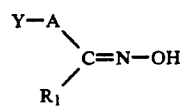

(VIII)

wherein Y, A and $R_1$ are as defined above, with imidazole, $C_1$-$C_4$ alkyl imidazole or a salt thereof, e.g. following for example the procedure in Arzneim. Forsch./Drug Res., 29(II), 1510-13, (1979).

In view of the oxime double bond, also an oxime of formula (II) may be obtained either as pure Z- or E-isomer or as a mixture thereof. Also an oxime of formula (II), if desired, can be submitted to the same isomerizations on the oxime double bond described above as to a compound of formula (I), according to known methods. Similarly, a mixture of Z- and E-isomers of an oxime of formula (II) can be separated into the single isomers by following customary methods.

The compounds of formula (III), (IV) and (V) are either known compounds or can be obtained by known methods from known compounds. Also the compounds of formula (VI) are either known compounds or can be obtained from known compounds by following known methods, e.g. those described in Tetrahedron (1967), 23, 4441, or in general described in Organic Functional Group Preparation, by S. R. Sandler and W. Karo, Vol. III, chapter X, Academic Press, (1972). The compounds of formula (VII) can be obtained by reaction of a known compound of formula (IX)

(IX)

wherein Q and Q' are as defined above, with a compound of formula (VI) as defined above, by following the same reaction procedures described above under process c).

Alternatively a compound of formula (VII) can be obtained from a compound of formula (IX), via the corresponding oxime of formula (X)

(X)

wherein Q and Q' are as defined above, by reaction either with a compound either of formula (III) or of formula (IV) by following the same reaction conditions described above under processes a) and b).

When in the compounds of the invention and in the intermediate products thereof groups are present which need to be protected during the reactions reported above, the groups can be protected in conventional way before the reaction takes place and then deprotected after its end, according to well known methods.

PHARMACOLOGY

We have found that the compounds of formula (I), and the pharmaceutically acceptable salts thereof are selective inhibitors of thromboxane $A_2$ (TxA$_2$) synthesis and are therefore useful in the treatment of diseases related in particular to an enhancement of TxA$_2$ synthesis in mammals, including humans.

The compounds of formula (I) were for example tested for their ability to inhibit TxA$_2$ Synthase activity (as reflected by TxB$_2$ generated in whole blood during clotting or in isolated glomeruli) in vitro in the rat.

The in vitro experiments were carried out as follows:

The effect of the compounds on TxA$_2$ synthesis was evaluated in serum.

Blood was withdrawn from the abdominal aorta of the animals under light ether anesthesia. The blood was immediately divided in portions of 0.5 ml and distributed in glass tubes each containing a concentration of the test compounds or of the reference compounds, i.e. Dazoxiben, which is thromboxane synthase inhibitor (Randall et al.-Thromb. Res. 23, 145, 1981) and Acetylsalicylic Acid (ASA), which is cyclooxygenase inhibitor.

Samples were then allowed to clot for 1 h at 37° C., centrifuged at 3000 rpm for 10 min, serum collected and stored at −20° C. until assayed. TxB$_2$ levels were determined by RIA according to previously described procedures [Patrono et al.—Thromb. Res. 17, 1, 317, 1980] using highly specific antibody.

The compounds of the invention showed remarkable activity in the above tests.

In particular for example, the compound of the invention (±)-(E)-5-[1-phenyl-2-(imidazol-1-yl)-2-(4-fluorobenzyl)ethylidene]aminoxypentanoic acid (internal code FCE 27317), was found to exhibit a marked inhibitory activity on TxA$_2$ synthesis significantly more potent than that of reference compounds Dazoxiben and ASA.

These results are summarized in Table 1.

TABLE 1

| In vitro effects on TxB$_2$ production in rat whole blood [Data are expressed as IC$_{50}$ (M) and limits for p = 0.95]. | |
|---|---|
| Compound | Whole Blood (n = 8) |
| FCE 27317 | 3.9 × 10$^{-7}$ (2.24–8.47 × 10$^{-7}$) |
| Dazoxiben | 1.2 × 10$^{-6}$ (0.70–1.9 × 10$^{-6}$) |
| ASA | 4.2 × 10$^{-5}$ (3.1–5.6 × 10$^{-5}$) |

Wherein n is the number of replicants.

The compounds of the invention, being able to inhibit selectively the formation of TxA$_2$, can be used as vasodilatory and antiaggregant agents, for example in all the cases of thrombosis, peripheral vasculopathies and coronary artery disease. In fact, inhibition of TxA$_2$ production reduces the probability of thrombi formation and of vasoconstriction with consequent ischemic events and leaving unaltered (or increasing) PGI$_2$ production, improves vasodilation, tissue blood supplies and protects the vessel wall.

Moreover, the compounds of the invention were tested for TxA$_2$ antagonism in a binding assay in washed human platelets, using as radiolabelled ligand [$^3$H]-SQ 29,548.

The experiments were carried out as follows:

Blood from healthy volunteers of both sexes who had not taken any medication for at least 10 days is collected into one-tenth volume of acid citrate dextrose containing indomethacin (28 μM). Platelet rich plasma (PRP), obtained by centrifugation of the blood at 200×g for 20 min, is washed twice (1000×g for 10 min). The platelets are then resuspended in Tyrode-Hepes buffer (pH 7.4) to a final concentration of 5–10×10$^{-8}$ cells/ml and incubated for 0–60 min at 25° C. with [$^3$H]-SQ 29,548 (5 nM). For displacement experiments various concentrations (10$^{-9}$–10$^{-4}$M) of competing ligands were added and incubated for 30 min at 25° C. Non-specific binding was determined in the presence of 50 μM U46619 and was approximately 5% of total binding of [$^3$H]-SQ 29,548. After incubation, 4 ml of ice-cold TRIS-HCl buffer (10 mM, pH 7.4) was added to each tube and the reaction mixture was immediately filtered by suction through a Whatman GE/C glass filter disc which was washed 2 times with ice-cold TRIS-HCl (4 ml) and counted for radioactivity by a Packard-β-counter.

The binding data were analysed by computerized non-linear curve fitting using the Ligand program and expressed as IC$_{50}$. In Table II, as an example, the result obtained with the compound of the invention (±)-(E)-5-[1-phenyl-2-(imidazol-1-yl)-2-(4-fluorobenzyl)ethylidene]aminoxypentanoic acid in the binding test is compared to that obtained with the reference standard compound Sulotroban (BM 13177) [DE-A-2,809,377].

This result shows that the compound of the invention FCE 27109, besides being active as TxA$_2$ synthase inhibitor, has also a good affinity for the receptor better than that showed by the known compound Sulotroban (BM 13177), which on the other hand is devoid of TxA$_2$ synthase inhibitory activity.

TABLE II

| $^3$H SQ 29,548 binding displacement (washed human platelets). IC$_{50}$ (M). | |
|---|---|
| BM 13177 | 7.3 × 10$^{-6}$ |
| FCE 27317 | 3.87 × 10$^{-8}$ (±0.30) |

Being the compounds of the present invention both TxA$_2$ synthase inhibitors and PGH$_2$ TxA$_2$ antagonists in the platelets on the basis of the state of the art, as reported e.g. in J. Clin. Invest. 80, 1435 (1987) and in Adm. Prostaglandins, Tromboxanes, Leukotrienes Res. Vol. 17 (1987) p. 49, these compounds result particularly suitable for the treatment of a disease state in which an enhancement of TxA$_2$ synthesis exerts a pathogenic effect, for instance in those mentioned above.

Another use of the compounds of the invention is for the treatment of migraine. As is known, for example, in the case of migraine it has been demonstrated a diffused vasoconstriction induced by platelet TxA$_2$ overproduction [J. Clin. Pathol. (1971), 24, 250; J. Headache (1977), 17, 101]. A platelet overproduction of TxA$_2$ and MDA (malondialdehyde) in diabetes mellitus has been demonstrated and correlated with microcirculatory defects in the illness [Metabolism (1979), 28, 394; Eu. J. Clin. Invest. (1979), 9, 223; Thrombosis Haemost. (1979), 42, 983; J. Lab. Clin. Med. (1981), 97, 87]. Therefore, the compounds of the invention can be used in the treatment of diabetes, in particular, diabetic microangiopathy.

Moreover, the compounds of the invention can be used as anti-inflammatory agents. As is known, for example, fluid obtained from carrageenin-induced granuloma converts arachidonic acid into TxA$_2$ in vitro and TxA$_2$ levels are increased in the synovial fluid of rheumatoid arthritis patients and in the fluid of carrageenin-induced inflammation in rats [Prostaglands (1977), 13, 17; Scand. J. Rheum. (1977), 6, 151]. Recently it has been also demonstrated that an overproduction of TxA$_2$ is involved in the pathogenesis of hypertension and that a specific inhibitor of TxA$_2$ production may be employed in hypertension (Eu. J. Pharmacol. (1981), 70, 247). In fact, the compounds of the invention can be used as hypotensive agents.

For example an increased $TxA_2$ synthesis and decreased prostacyclin synthesis are reported in pregnancy-induced hypertension [Am. J. Obstet. Gynecol. (1987), 157, 325; Hypertension (1988), 11, 550]. Treatment with thromboxane synthase inhibitors is therefore useful in this pathology. Furthermore it has been shown a role of $TxA_2$ in the pathogenesis of ulcerative disorders of the stomach in accordance with its powerful gastric vasoconstrictory activity, so that also in this field a $TxA_2$ inhibitor is useful [Nature (1981), 202, 472]. In fact, the compounds of the invention are indicated for the treatment of peptic ulcers. The compounds of the invention can be also antitumoral agents. It is known, for example, that a selective inhibition of $TxA_2$ synthesis has been demonstrated to reduce the number of lung metastases and to slow down tumor growth [Nature (1982), 295, 188].

In view of the correlation between $TxA_2$ synthesis and calcium transport, recently showed by some authors, specific $TxA_2$ synthetase inhibitors, such as the compounds of the invention, can also find use in the treatment of osteoporosis, e.g. post-menopausal osteoporosis [Prostaglandins (1981), 21, 401].

Moreover, the compounds of the invention are indicated for the treatment of angina pectoris and heart failure. In this respect, it is known, for example, that high levels of $TxB_2$ have been found in patients with Prinzmetal's angina [Prostaglandins and Med. (1979), 2, 243] and in patients with recurrent angina attacks [Sixth Intern. Congress on Thrombosis, Monte Carlo October, 1980 Abs No. 140]. The platelet antiaggregatory activity of the compounds of the invention was evaluated in vitro and in vivo, for example, according to the modified methods of Born [Born G.V.R., Nature 194, 927 (1962)] and Silver [Silver M. J., Science 183, 1085 (1974)].

The compounds of this invention were found in vitro to have inhibitory activity on platelet aggregation induced by collagen or ADP (adenosine-5'-diphosphate) in platelet rich plasma of guinea pig [Dunkin Hantley Iva: PDH (SPF) Ivanovas GmbH, Germany].

Therefore the compounds of the invention may be useful in preventing or reducing platelet loss during extracorporeal circulation; for example during coronary artery bypass and graft procedures or during kidney dialysis. It has been, moreover, shown that circulatory shock, for example endotoxic and haemorrhagic shock, is associated with increased $TxA_2$ synthesis so that the compounds of the invention can be useful in these pathologies. Moreover, the compounds of the present invention can also be useful for the treatment of bronchial hyperreactivity in the therapy of asthma.

A role for $TxA_2$ in asthma can be inferred on the basis of its bronchoconstrictory activity in experimental animal models [Br. J. Pharmacol. (1984), 82 (3), 565]. An inhibitory activity of bronchospasm induced by Platelet Activating Factor (PAF) in rats is also reported, e.g. for the $TxA_2$ synthetase inhibitors described in GB-B-2205494.

The compounds of the present invention can also find use in the treatment of nephropathies e.g. forms of glomerulonephritis, diabetic nephropathy or nephropathies secondary to systemic lupus erithematous (SLE), and in the prevention and/or treatment of Cyclosporin A-induced nephrosis. Accordingly, the compounds of this invention can also be used for preventing and/or treating toxemia during pregnancy, typically preeclampsia, eclampsia and preeclamptic (eclamptic, eclamptogenic) toxemia.

Recently a positive correlation between enhanced intrarenal synthesis of $TxA_2$ and the progression of chronic glomerular disease has been demonstrated in different animal models of immune and non-immune renal damage and in humans [J. Clin. Invest. (1985) 75, 94; J. Clin. Invest. (1985), 76, 1011]. Accordingly, the $TxA_2$ synthase inhibitors recently described e.g. in GB-B-2205240 were found to be active in reducing proteinuria and creatinine serum levels in the doxorubicin induced nephrosis in rats and in reducing proteinuria and increasing the glomerular filtration rate (GFR) in the spontaneous focal glomerulosclerosis in the Milan Normotensive Strain (MNS) rats.

In particular in the treatment of renal failure the compounds of the invention may be used in association with an angiotensin converting enzyme inhibitor (ACEI), both as separated and substantially concomitant administration. The compounds of the invention can also be used to prevent or treat cyclosporin A-induced nephrosis in mammals.

The compounds of the invention may be also used to inhibit the renal and cardiac transplant rejection. In fact, after transplantation increased urinary $TxB_2$ excretion or whole blood $TxA_2$ synthesis have been reported both in man and rats [Lancet (1981), ii, 431; Transplantation (1987), 43, 346]. Another use of the compounds of the present invention is in the treatment of hyperlipidaemia, namely hypercholesterolaemia and hypertriglyceridaemia secondary to nephrotic syndrome.

Hyperlipidaemia is a common feature of nephrotic syndrome in man [New Engl. J. Med. (1983), 312 (24), 1544] and in addition elevated triglycerides and cholesterol levels are reported in animal models such as doxorubicin induced nephrotic syndrome [Expt. Mol. Pathology (1983), 39, 282]; elevated urinary albumin excretion has been suggested as the pathogenetic mechanisms [Kidney International (1987), 32, 813]. Also $TxA_2$ synthase inhibitors recently described in GB-B-2205240, e.g. proved to be active in reducing cholesterol and triglycerides in aged Milan Normotensive Strain rats and in reducing triglycerides in doxorubicin treated rats.

It has also been shown that in cholesterol fed rabbit, an animal model of diet induced atherosclerosis, arachidonic acid metabolism is an important factor in early lesion development. In particular a shift in metabolism from $TxA_2$ to $PGE_2$ may suppress lesion development (i.e. atheromatous plaque) in hypercholesterolaemia.

The compounds of the invention can be therefore used in this pathology.

The compounds of the invention can also be used in association with thrombolytic agents (e.g. tPA, Streptokinase, proUrokinase), in order to reduce the dose of the latter required in thrombolytic therapy, and to lower the incidence of reocclusion and possibly haemorrhage.

A further application of the compounds of the invention is the prevention and/or treatment of restenosis after percutaneous transluminal angioplasty.

The toxicity of the compounds of the invention is negligible, therefore they can be safely used in therapy. Mice and rats which had been deprived of food for nine hours were treated orally with single administrations of increasing doses of compounds of the invention, then housed and normally fed. The orientative acute toxicity ($LD_{50}$) was assessed on the seventh day after the treatment.

In view of their high activity and low toxicity, the compounds of the invention can be safely used in medicine. The therapeutic regimen for the different clinical syndromes must be adapted to the type of pathology, taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute pathological states.

For maintenance regimens the oral or parenteral, e.g. intramuscular, route is preferred.

The dosage level suitable for oral administration to adult humans of the compounds of the invention e.g. ($\pm$)-(E)-5-[1-phenyl-2-(imidazol-1-yl)-2-(4-fluorobenzyl)ethylidene]aminoxypentanoic acid may range from about 50 mg to about 300 mg per dose, 1 to 3 times a day.

Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions, tablets, pills, gelatine capsules, syrups, drops or suppositiries.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or the may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrups, emulsions and suspensions. The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and, if desired, a suitable amount of lidocaine hydrochloride. The solutions for intravenous injection or infusion may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the present invention.

EXAMPLE 1

To a stirred mixture of 3.08 g (0.01 moles) of ($\pm$) (E+Z)-1-phenyl-2-(imidazol-1-yl)-2-(4-fluorobenzyl)ethanone oxime and 10 ml of dimethylformamide, 0.44 g (0.01 moles) of sodium hydride dispersion 55% are added portionwise at room temperature. Upon completion, stirring is continued till hydrogen evolution stops. Then 2.09 g (0.01 moles) of ethyl 5-bromopentanoate are added at room temperature and stirring is continued for 6 hours. The reaction mixture is diluted with water and extracted twice with ethyl acetate. The organic phase is washed with water and with saturated sodium chloride solution, dried over anhydrous $Na_2SO_4$ and evaporated to dryness. The residue is purified by column chromatography over silica gel (eluant: dichloromethane/methanol=190/10) yielding 4.13 g (94%) of ethyl ($\pm$) (E+Z)-5-[1-phenyl-2-(imidazol-1-yl)-2-(4-fluorobenzyl)ethylidene]aminoxypentanoate.

Microanalysis

Found: C 67.26; H 6.31; N 9.38; F 4.25. Calculated for $C_{25}H_{28}FN_3O_3$: C 68.63; H 6.45; N 9.60; F 4.34.

NMR ($CDCl_3$)

5.06 (1H, dd, CH—N=, E isomer). 6.02 (1H, t, CH—N, Z isomer).

EXAMPLE 2

To a stirred solution of 2 g (0.00457 moles) of ethyl ($\pm$) (E+Z)-5-[1-phenyl-2-(imidazol)-1-yl)-2-(4-fluorobenzyl)ethylidene]aminoxypentanoate in 50 ml of ethanol, 20 ml aqueous hydroxide 1N are added at room temperature. Stirring is continued for 4 hrs at room temperature and then ethanol is removed under vacuum. The aqueous solution is acidified with acetic acid till pH 5 with external cooling and extracted three times with ethyl acetate.

The organic phase is washed with water, with saturated sodium chloride solution, dried over anhydrous $Na_2SO_4$ and evaporated to dryness. The residue is purified by column chromatography over silica gel (eluant: chloroform/methanol=185/15) yielding 1.02 g of ($\pm$) (E)-5-[1-phenyl-2-(imidazol-1-yl)-2-(4-fluorobenzyl)ethylidene]aminoxypentanoic acid and 0.48 g of the corresponding "Z" isomer.

($\pm$) (E)-5-[1-phenyl-2-(imidazol-1-yl)-2-(4-fluorobenzyl)ethylidene]aminoxypentanoic acid:
m.p. 132°-3° C. (Solvent: diisopropyl ether)

($\pm$) (Z)-5-[1-phenyl-2-(imidazol-1-yl)-2-(4-fluorobenzyl)ethylidene]aminoxypentanoic acid:
m.p.: 94°-6° C. (Solvent: diisopropyl ether).

Microanalysis

Found: C 67.64; H 6.02; N 10.37; F 4.54. Calculated for $C_{23}H_{24}FN_3O_3$: C 67.47; H 5.91; N 10.26; F 4.64.

By the same procedure starting from the corresponding ($\pm$) (E+Z) ethyl aminoxypentanoate the following compounds can be prepared:
($\pm$) (E)-5-[1-phenyl-2-(imidazol-1-yl)-2-(4-chlorobenzyl)ethylidene]aminoxypentanoic acid:
m.p. 110°-112° C.

Microanalysis

Found: C 64.45; H 5.68; N 9.90; Cl 8.45. Calculated for $C_{23}H_{24}ClN_3O_3$: C 64.86; H 5.68; N 9.86; Cl 8.32.

(±) (Z)-5-[1-phenyl-2-(imidazol-1-yl)-2-(4-chlorobenzyl)ethylidene]aminoxypentanoic acid:
m.p. 112°–115° C.

Microanalysis

Found: C 64.70; H 5.64; N 10.02; Cl 8.39. Calculated for $C_{23}H_{24}ClN_3O_3$: C 64.86; H 5.68; N 9.86; Cl 8.32.

(±) (E)-5-[1-cyclohexyl-2-(imidazol-1-yl)-2-(3-fluorobenzyl)ethylidene]aminoxypentanoic acid:

Microanalysis

Found: C 66.18; H 7.58; N 9.89; F 4.21. Calculated for $C_{23}H_{30}FN_3O_3$: C 66.49; H 7.28; N 10.11; F 4.57.

NMR (CDCl₃)

4.8 (1H, d.d, —CH—N=).

(±) (Z)-5-[1-cyclohexyl-2-(imidazol-1-yl)-2-(3-fluorobenzyl)ethylidene]aminoxypentanoic acid:

Microanalysis

Found: C 65.66; H 7.48; N 8.55. Calculated for $C_{23}H_{30}FN_3O_3$: C 66.49; H 7.28; N 10.11.

NMR (CDCl₃)

5.55 (1H, m, —CH—N=).

(±) (E)-5-[1-cyclohexyl-2-(imidazol-1-yl)-2-(4-methoxybenzyl)ethylidene]aminoxypentanoic acid:
m.p.: 153°–155° C.

Microanalysis

Found: C 67.00; H 7.76; N 9.69. Calculated for $C_{24}H_{33}N_3O_4$: C 67.42; H 7.78; N 9.83.

(±) (Z)-5-[1-cyclohexyl-2-(imidazol-1-yl)-2-(4-methoxybenzyl)ethylidene]aminoxypentanoic acid:
m.p. 124°–127° C.

Microanalysis

Found: C 67.06; H 7.86; N 9.61. Calculated for $C_{24}H_{33}N_3O_4$: C 67.42; H 7.78; N 9.89.

(±) (E)-5-[1-cyclohexyl-2-(imidazol-1-yl)-2-(benzylethylidene]-2,2-dimethylaminoxy]pentanoic acid:

Microanalysis

Found: C 69.85; H 8.16; N 9.77. Calculated for $C_{25}H_{35}N_3O_3$: C 70.56; H 8.29; N 9.87.

NMR (CDCl₃)

| | |
|---|---|
| 1.1–1.9 | (20H, m, —O—CH₂—C$\underline{H}_2$—C$\underline{H}_2$— + C$\underline{H}_2$ at 2, 3, 4, 5 and 6 positions of cyclohexyl ring + —CH₂—C(C$\underline{H}_3$)₂—(COOH) |
| 2.95–3.4 | (3H, m, Ph—C$\underline{H}_2$ + CH at 1 position of cyclohexyl ring) |
| 4.15 | (2H, m, —O—C$\underline{H}_2$—CH₂) |
| 4.85 | (1H, d.d, —C$\underline{H}$—N=) |
| 6.9–7.2 | (7H, m, phenyl ring + C$\underline{H}$ at 4 and 5 positions of imidazole ring) |
| 7.58 | (1H, bs, N=C$\underline{H}$—N—) |

(±) (Z)-5-[1-phenyl-2-(imidazol-1-yl)-2-benzylethylidene]-3,3-dimethylaminoxypentanoic acid:

Microanalysis

Found: C 71.65; H 7.07; N 9.96. Calculated for $C_{25}H_{29}N_3O_3$: C 71.57; H 6.97; N 10.01.

NMR (CDCl₃)

5.85 (1H,b.t, —CH—N=).

(±) (E)-5-[1-phenyl-2-(imidazol-1-yl)-2-benzylethylidene]-3,3-dimethylaminoxypentanoic acid:
m.p.: 122°–4° C.

Microanalysis

Found: C 70.44; H 7.32; N 9.25. Calculated for $C_{25}H_{29}N_3O_3$: C 71.57; H 6.97; N 10.01.

(±) (Z)-5-[1-phenyl-2-(imidazol-1-yl)-2-benzylethylidene]-2,2-dimethylaminoxypentanoic acid:
m.p. 158°–9° C.

Microanalysis

Found: C 70.68; H 7.04; N 9.65. Calculated for $C_{25}H_{29}N_3O_3$: C 71.57; H 6.97; N 10.0.

(±) (E)-5-[1-phenyl-2-(imidazol-1-yl)-2-benzylethylidene]-2,2-dimethylaminoxypentanoic acid:
m.p.: 138°–140° C.

Microanalysis

Found: C 71.34; H 7.03; N 9.77. Calculated for $C_{25}H_{29}N_3O_3$: C 71.57; H 6.97; N 10.01.

(±) (Z)-5-[1-cyclohexyl-2-(imidazol-1-yl)-2-(4-methylsulfonylbenzyl)ethylidene]aminoxypentanoic acid:
m.p.: 72°–76° C.

Microanalysis

Found: C 59.94; H 7.03; N 8.55; S 6.3. Calculated for $C_{24}H_{33}N_3O_5S$: C 60.61; H 6.99; N 8.83; S 6.74.

(±) (E)-5-[1-cyclohexyl-2-(imidazol-1-yl)-2-(4-methylsulfonylbenzyl)ethylidene]aminoxypentanoic acid:
m.p.: 78°–83° C.

Microanalysis

Found: C 60.02; H 6.99; N 8.83; S 6.74. Calculated for $C_{24}H_{33}N_3O_5S$: C 60.61; H 6.99; N 8.83; S 6.74.

(±) (Z)-5-[1-(3-trifluoromethylphenyl)-2-(imidazol-1-yl)-2-benzylethylidene]aminoxypentanoic acid:

Microanalysis

Found: C 62.40; H 5.42; N 8.58. Calculated for $C_{24}H_{24}F_3N_3O_3$: C 62.74; H 5.26; N 9.25.

NMR (CDCl₃)

6.00 (1H, t, —CH—N=).

(±) (E)-5-[1-(3-trifluoromethylphenyl)-2-(imidazol-1-yl)-2-benzylethylidene]aminoxypentanoic acid:
m.p.: 114°–116° C.

Microanalysis

Found: C 62.75; H 5.36; N 8.93. Calculated for $C_{24}H_{24}F_3N_3O_3$: C 62.74; H 5.26; N 9.25.

(±) (Z)-5-[1-(4-methoxyphenyl)-2-(imidazol-1-yl)-2-(4-fluorophenyl)ethylidene]aminoxypentanoic acid:

Microanalysis

Found: C 64.63; H 6.12; N 9.78; F 4.42. Calculated for $C_{24}H_{26}FN_3O_4$: C 65.59; H 5.96; N 9.56; F 4.32.

NMR (CDCl₃)

5.95 (1H, d.d, —CH—N=).

(±) (E)-5-[1-(4-methoxyphenyl)-2-(imidazol-1-yl)-2-(4-fluorophenyl)ethylidene]aminoxypentanoic acid:

Microanalysis

Found: C 64.63; H 6.12; N 9.78; F 4.24. Calculated for C₂₄H₂₆FN₃O₄: C 65.59; H 5.96; N 9.56; F 4.32.

NMR (CDCl₃)

5.05 (1H, d.d., —CH—N=).

(±) (Z)-5-[1-cyclohexyl-2-(imidazol-1-yl)-2-(3-chlorobenzyl)ethylidene]aminoxypentanoic acid:

Microanalysis

Found: C 63.01; H 6.80; N 9.15; Cl 8.54. Calculated for C₂₃H₃₀ClN₃O₃: C 63.95; H 7.00. N 9.73; Cl 8.21.

NMR (CDCl₃)

5.55 (1H, d.d., —CH—N=).

(±) (E)-5-[1-cyclohexyl-2-(imidazol-1-yl)-2-(3-chlorobenzyl)ethylidene]aminoxypentanoic acid:

Microanalysis

Found: C 63.47; H 6.95; N 9.42; Cl 8.38. Calculated for C₂₃H₃₀ClN₃O₃: C 63.95; H 7.00; N 9.73; Cl 8.21.

NMR (CDCl₃)

4.80 (1H,d.d., —CH—N=).

(±) (E)-5-[1-cyclohexyl-2-(imidazol-1-yl)-2-(4-trifluoromethylbenzyl)ethylidene]aminoxypentanoic acid:

Microanalysis

Found: C 61.42; H 6.65; N 8.82; F 12.53. Calculated for C₂₄H₃₀F₃N₃O₃: C 61.92; H 6.40; N 9.02; F 12.26.

NMR (CDCl₃)

4.85 (1H, d.d., —CH—N=)

(±) (E)-5-[1-(4-chlorophenyl)-2-(imidazol-1-yl)-2-(4-fluorobenzyl)ethylidene]aminoxypentanoic acid:

Microanalysis

Found: C 61.15; H 5.32; N 9.83; Cl 7.92. Calculated for C₂₃H₂₃Cl F N₃O₃: C 62.23; H 5.22; N 9.46; Cl 7.98.

NMR (CDCl₃)

5.05 (1H, d.d., —CH—N=)

(±) (E)-5-[1-cyclohexyl-2-(imidazol-1-yl)-2-benzylethylidene]-3,3-dimethylaminoxypentanoic acid:
m.p.: 116°-118° C.

Microanalysis

Found: C 69.84; H 8.26; N 9.71. Calculated for C₂₅H₃₅N₃O₃: C 70.55; H 8.29; N 9.87.

(±) (Z)-5-[1-cyclohexyl-2-(imidazol-1-yl)-2-benzylethylidene]-3,3-dimethylaminoxypentanoic acid, hydrochloride.

Microanalysis

Found: C 64.52; H 7.80; N 8.82. Calculated for C₂₅H₃₆Cl N₃O₃: C 64.44; H 7.85; N 9.09.

NMR (CDCl₃)

5.35 (1H, d.d., —CH—N=).

(±) (E)-5-[1-n.hexyl-2-(imidazol-1-yl)-2-benzylethylidene]aminoxypentanoic acid:

Microanalysis

Found: C 69.28; H 8.30; N 10.42. Calculated for C₂₃H₃₃N₃O₃: C 69.14; H 8.32; N 10.52.

NMR (CDCl₃)

4.8 (1H, d.d., —CH—N=).

(±) (E)-5-[1-methyl-2-(imidazol-1-yl)-2-benzylethylidene]aminoxypentanoic acid.

Microanalysis

Found: C 65.02; H 6.99; N 12.59. Calculated for C₁₈H₂₃N₃O₃: C 65.63; H 7.03; N 12.75.

NMR (CDCl₃)

4.85 (1H, d.d., —CH—N=).

(±) (E)-5-[1-methyl-2-imidazol-1-yl)-2-(4-fluorobenzyl)ethylidene]aminoxypentanoic acid:

Microanalysis

Found: C 62.05; H 6.31; N 11.98; F 5.27. Calculated for C₁₈H₂₂FN₃O₃: C 62.23; H 6.38; N 12.09; F 5.47.

NMR (CDCl₃)

4.9 (1H, d.d., —CH—N=).

and analogously:

(±) (Z)-5-[1-cyclohexyl-2-(imidazol-1-yl)-2-(3-fluorobenzyl)ethylidene]aminoxypentanoic acid;

(±) (Z)-5-[1-cyclohexyl-2-(imidazol-1-yl)-2-(4-trifluoromethylbenzyl)ethylidene]aminoxypentanoic acid;

(±) (E)-5-[1-(4-fluorophenyl)-2-(imidazol-1-yl)-2-(3-chlorobenzyl)ethylidene]aminoxypentanoic acid;

(±) (Z)-5-[1-(4-fluorophenyl)-2-(imidazol-1-yl)-2-(3-chlorobenzyl)ethylidene]aminoxypentanoic acid;

(±) (E)-5-[1-(3-trifluoromethylphenyl)-2-(imidazol-1-yl)-2-(4-fluorobenzyl)ethylidene]aminoxypentanoic acid;

(±) (Z)-5-[1-(3-trifluoromethylphenyl)-2-(imidazol-1-yl)-2-(4-fluorobenzyl)ethylidene]aminoxypentanoic acid;

(±) (E)-5-[1-(3-methylsulfonylphenyl)-2-(imidazol-1-yl)-2-(3-fluorobenzyl)ethylidene]aminoxypentanoic acid;

(±) (Z)-5-[1-(3-methylsulfonylphenyl)-2-(imidazol-1-yl)-2-(3-fluorobenzyl)ethylidene]aminoxypentanoic acid;

(±) (E)-5-[1-(4-methylsulfonylphenyl)-2-(imidazol-1-yl)-2-(4-fluorobenzyl)ethylidene]aminoxypentanoic acid;

(±) (Z)-5-[1-(4-methylsulfonylphenyl)-2-(imidazol-1-yl)-2-(4-fluorobenzyl)ethylidene]aminoxypentanoic acid;

(±) (Z)-5-[1-cyclohexyl-2-(imidazol-1-yl)-2-benzylethylidene]2,2-dimethyl aminoxypentanoic acid;

(±) (E)-5-[1-(4-fluorophenyl)-2-(imidazol-1-yl)-2-(4-methylsulfonylbenzyl)ethylidene]aminoxypentanoic acid;

(±) (Z)-5-[1-(4-fluorophenyl)-2-(imidazol-1-yl)-2-(4-methylsulfonylbenzyl)ethylidene]aminoxypentanoic acid;

(±) (Z)-5-[1-n.hexyl-2-(imidazol-1-yl)-2-benzylethylidene]aminoxypentanoic acid;

(±) (Z)-5-[1-methyl-2-(imidazol-1-yl)-2-benzylethylidene]aminoxypentanoic acid;

(±) (Z)-5-[1-methyl-2-(imidazol-1-yl)-2-(4-fluorobenzyl)ethylidene]aminoxypentanoic acid;

(±) (E)-5-[1-ethyl-2-(imidazol-1-yl)-2-benzylethylidene]aminoxypentanoic acid;

(±) (Z)-5-[1-ethyl-2-(imidazol-1-yl)-2-benzylethylidene]aminoxypentanoic acid;
(±) (E)-5-[1-propyl-2-(imidazol-1-yl)-2-benzylethylidene]aminoxypentanoic acid; and
(±) (Z)-5-[1-propyl-2-(imidazol-1-yl)-2-benzylethylidene]aminoxypentanoic acid.

EXAMPLE 3

To a stirred solution of 0.169 g (0.00055 moles) of [1-cyclohexyl-2-(imidazol-1-yl)-2-(4-methoxybenzyl)ethanone] in 15 ml of pyridine, 0.21 g (0.00135 moles) of 5-aminoxypentanoic acid hydrochloride are added at room temperature.

Stirring is continued for 12 hours.

The reaction mixture is evaporated under vacuum, dilute with water and acidified with acetic acid till pH=5.

The aqueous solution is extracted with methylene chloride dried and evaporated. The residue is purified by column chromatography over silica gel (eluant: methylenechloride/ethanol=95/5).

The pure, fractions are collected and evaporated, yielding 0.102 g of (±) (E)-5-[1-cyclohexyl-2-(imidazol-1-yl)-2-(4-methoxybenzyl)ethylidene]aminoxypentanoic acid and 0.036 g of the corresponding "Z" isomer.

(±) (E)-5-[1-cyclohexyl-2-(imidazol-1-yl)-2-(4-methoxybenzyl)ethylidene]aminoxypentanoic acid:
m.p. 154°–155° C.

Microanalysis

Found: C 67.14; H 7.70; N 9.49. Calculated for $C_{24}H_{33}N_3O_4$: C 67.42; H 7.78; N 9.83.

(±) (Z)-5-[1-cyclohexyl-2-(imidazol-1-yl)-2-(4-methoxybenzyl)ethylidene]aminoxypentanoic acid:
m.p. 125°–126° C.

Microanalysis

Found: C 67.09; H 7.66; N 9.73. Calculated for $C_{24}H_{33}N_3O_4$: C 67.42; H 7.78; N 9.83.

By the same procedure, the following compounds can be prepared:
(±) (E)-5-[1-cyclohexyl-2-(imidazol-1-yl)-2-(3-fluorobenzyl)ethylidene]aminoxypentanoic acid;
(±) (Z)-5-[1-cyclohexyl-2-(imidazol-1-yl)-2-(3-fluorobenzyl)ethylidene]aminoxypentanoic acid;
(±) (E)-5-[1-phenyl-2-(imidazol-1-yl)-2-(4-chlorobenzyl)ethylidene]aminoxypentanoic acid;
(±) (Z)-5-[1-phenyl-2-(imidazol-1-yl)-2-(4-chlorobenzyl)ethylidene]aminoxypentanoic acid;
(±) (E)-5-[1-cyclohexyl-2-(imidazol-1-yl)-2-(4-trifluoromethylbenzyl)ethylidene]aminoxypentanoic acid; and
(±) (Z)-5-[1-cyclohexyl-2-(imidazol-1-yl)-2-(4-trifluoromethylbenzyl)ethylidene]aminoxypentanoic acid.

EXAMPLE 4

To a stirred solution of 1 g (0.0005 moles) of (±) (E)-5-[1-phenyl-2-(imidazol-1-yl)-2-(4-fluorobenzyl)ethylidene] aminoxypentanoic acid in 10 ml of methanol, 820 mg (0.015 moles) of a sodium methoxide solution in methanol are added. The reaction mixture is evaporated and the precipitate product is filtered off and dried yielding 970 mg (60%) of sodium (±)(E)-5-[1-phenyl-2-(imidazol-1-yl)-2-(4-fluorobenzyl)ethylidene]aminoxypentanoate.

EXAMPLE 5

Tablets, each weighing 150 mg and containing 50 mg of the active substance can be manufactured as follows:

| Composition (for 10,000 tablets) | |
|---|---|
| (±) (E) -5-[1-phenyl-2-(imidazol-1-yl)-2-(4-fluorobenzyl)ethylidene]aminoxypentanoic acid | 500 g |
| Lactose | 710 g |
| Corn starch | 237.5 g |
| Talc powder | 37.5 g |
| Magnesium stearate | 15 g |

(±)(E)-5-[1-phenyl-2-(imidazol)-1-yl)-2-(4-fluorobenzyl)ethylidene]aminoxypentanoic acid, lactose and a half of the corn starch are mixed: the mixture is then forced through a sieve of 0.5 mm openings. Corn starch (18 mg) is suspended in warm water (180 ml). The resulting paste is used to granulate the powder.

The granules are dried, comminuted on a sieve of sieve size 1.4 mm, the remaining quantity of starch, talc and magnesium are added, carefully mixed, and processed into tablets using punches of 8 mm diameter.

We claim:

1. A compound of formula (I)

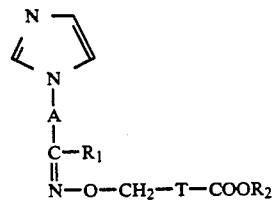

wherein
A is a divalent group of formula

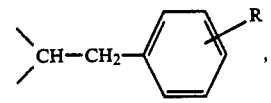

in which
R is hydrogen, halogen, $CF_3$, $C_1-C_4$ alkoxy, $C_1-C_4$ alkylsulfonyl or cyano;
$R_1$ is a) phenyl unsubstituted or substituted by halogen, $C_1-C_4$ alkoxy, $CF_3$ or $C_1-C_4$ alkylsulfonyl; b) cyclohexyl; or c) a straight or branched $C_1-C_6$ alkyl group;
T is a branched or straight $C_3-C_5$ alkylene chain;
$R_2$ is hydrogen or $C_1-C_4$ alkyl; or the pharmaceutically acceptable salts thereof.

2. A compound selected from the group consisting of:
(±)-5-[1-phenyl-2-(imidazol-1-yl)-2-(4-fluorobenzyl)ethylidene]aminoxypentanoic acid;
(±)-5-[1-phenyl-2-(imidazol-1-yl)-2-(4-chlorobenzyl)ethylidene]aminoxypentanoic acid;
(±)-5-[1-cyclohexyl-2-(imidazol-1-yl)-2-(3-fluorobenzyl)ethylidene]aminoxypentanoic acid;
(±)-5-[1-cyclohexyl-2-(imidazol-1-yl)-2-(4-methoxybenzyl)ethylidene]aminoxypentanoic acid;
(±)-5-[1-cyclohexyl-2-(imidazol-1-yl)-2-(4-trifluoromethylbenzyl)ethylidene]aminoxypentanoic acid;

(±)-5-[1-cyclohexyl-2-(imidazol-1-yl)-2-(3-chlorobenzyl)ethylidene]aminoxypentanoic acid;
(±)-5-[1-(4-fluorophenyl)-2-(imidazol-1-yl)-2-(3-chlorobenzyl)ethylidene]aminoxypentanoic acid;
(±)-5-[1-(3-trifluoromethylphenyl)-2-(imidazol-1-yl)-2-(4-fluorobenzyl)ethylidene]aminoxypentanoic acid;
(±)-5-[1-(3-methylsulfonylphenyl)-2-(imidazol-1-yl)-2-(3-fluorobenzyl)ethylidene]aminoxypentanoic acid;
(±)-5-[1-(4-methylsulfonylphenyl)-2-(imidazol-1-yl)-2-(4-fluorobenzyl)ethylidene]aminoxypentanoic acid;
(±)-5-[1-cyclohexyl-2-(imidazol-1-yl)-2-benzylethylidene]-2,2-dimethylaminoxypentanoic acid;
(±)-5-[1-cyclohexyl-2-(imidazol-1-yl)-2-benzylethylidene]-3,3-dimethylaminoxypentanoic acid;
(±)-5-[1-cyclohexyl-2-(imidazol-1-yl)-2-(4-methylsulfonylbenzyl)ethylidene]aminoxypentanoic acid;
(±)-5-[1-(4-fluorophenyl)-2-(imidazol-1-yl)-2-(4-methylsulfonylbenzyl)ethylidene]aminoxypentanoic acid;
(±)-5-[1-phenyl-2-(imidazol-1-yl)-2-benzylethylidene]-3,3-dimethylaminoxypentanoic acid;
(±)-5-[1-(3-trifluoromethylphenyl)-2-(imidazol-1-yl)-2-benzylethylidene]aminoxypentanoic acid;
(±)-5-[1-phenyl-2-(imidazol-1-yl)-2-benzylethylidene]-2,2-dimethylaminoxypentanoic acid;
(±)-5-[1-(4-methoxyphenyl)-2-(imidazol-1-yl)-2-(4-fluorobenzyl)ethylidene]aminoxypentanoic acid;
(±)-5-[1-(4-chlorophenyl)-2-(imidazol-1-yl)-2-(4-fluorobenzyl)ethylidene]aminoxypentanoic acid;
(±)-5-[1-n.hexyl-2-(imidazol-1-yl)-2-benzylethylidene]aminoxypentanoic acid;
(±)-5-[1-methyl-2-(imidazol-1-yl)-2-benzylethylidene]aminoxypentanoic acid;
(±)-5-[1-methyl-2-(imidazol-1-yl)-2-(4-fluorobenzyl)ethylidene]aminoxypentanoic acid;
(±)-5-[1-ethyl-2-(imidazol-1-yl)-2-benzylethylidene]aminoxypentanoic acid;
(±)-5-[1-propyl-2-(imidazol-1-yl)-2-benzylethylidene]aminoxypentanoic acid,
or the pharmaceutically acceptable salts thereof, either as Z- or E- isomer or Z,E-mixtures of said isomers.

3. A pharmaceutical composition comprising a suitable carrier and/or diluent and, as an active principle, a compound of formula (I) as defined in claim 1 or a pharmaceutically acceptable salt thereof in an amount which is effective for the treatment of a disease state involving an enhancement of thromboxane $A_2$ synthesis.

* * * * *